United States Patent [19]

Weiss

[11] 4,322,568
[45] Mar. 30, 1982

[54] GLYCOLALDEHYDE OR ETHYLENE GLYCOL FROM FORMALDEHYDE

[76] Inventor: Alvin H. Weiss, 26 Oakland Ave., Shrewsbury, Mass. 01545

[21] Appl. No.: 171,744

[22] Filed: Jul. 24, 1980

Related U.S. Application Data

[62] Division of Ser. No. 38,794, May 14, 1979, Pat. No. 4,238,418.

[51] Int. Cl.³ ............................................. C07C 29/14
[52] U.S. Cl. .................................................... 568/862
[58] Field of Search .......................................... 568/862

[56] References Cited

U.S. PATENT DOCUMENTS

| | | | |
|---|---|---|---|
| 1,213,740 | 1/1917 | Calvert | 568/472 |
| 1,569,775 | 1/1926 | Mittasch et al. | 260/449.5 |
| 2,224,910 | 12/1940 | Hanford et al. | 568/862 |
| 2,760,983 | 8/1956 | MacLean et al. | 568/862 |
| 4,200,765 | 4/1980 | Goetz | 568/862 |

Primary Examiner—Joseph E. Evans
Attorney, Agent, or Firm—Blodgett & Blodgett

[57] ABSTRACT

An aqueous 30 wt. % solution of formaldehyde trickled with an equal volume of NaOH solution over a zeolite (NaX, 5 A, or Na Mordenite) at 94° C., 1 atm, 1.21-2.36 liquid hourly space velocity, catalytically condenses to $HOCH_2CHO$, glycolaldehyde, a fraction of which then converts to $HOCH_2CH_2OH$, ethylene glycol, by cross-Cannizzaro side reaction. Zeolite degradation is prevented by maintaining pH near 11. Selectivity can be controlled so that less than 1% byproduct formose sugars are made. Methanol and sodium formate are also byproducts. All of the remaining glycolaldehyde could, in principle, be converted to ethylene glycol in either a subsequent cross-Cannizzaro reaction or a hydrogenation step. Thus, the reaction represents a potential non-petrochemical route for either glycolaldehyde or ethylene glycol from $CO+H_2$, via methanol and formaldehyde.

8 Claims, 6 Drawing Figures

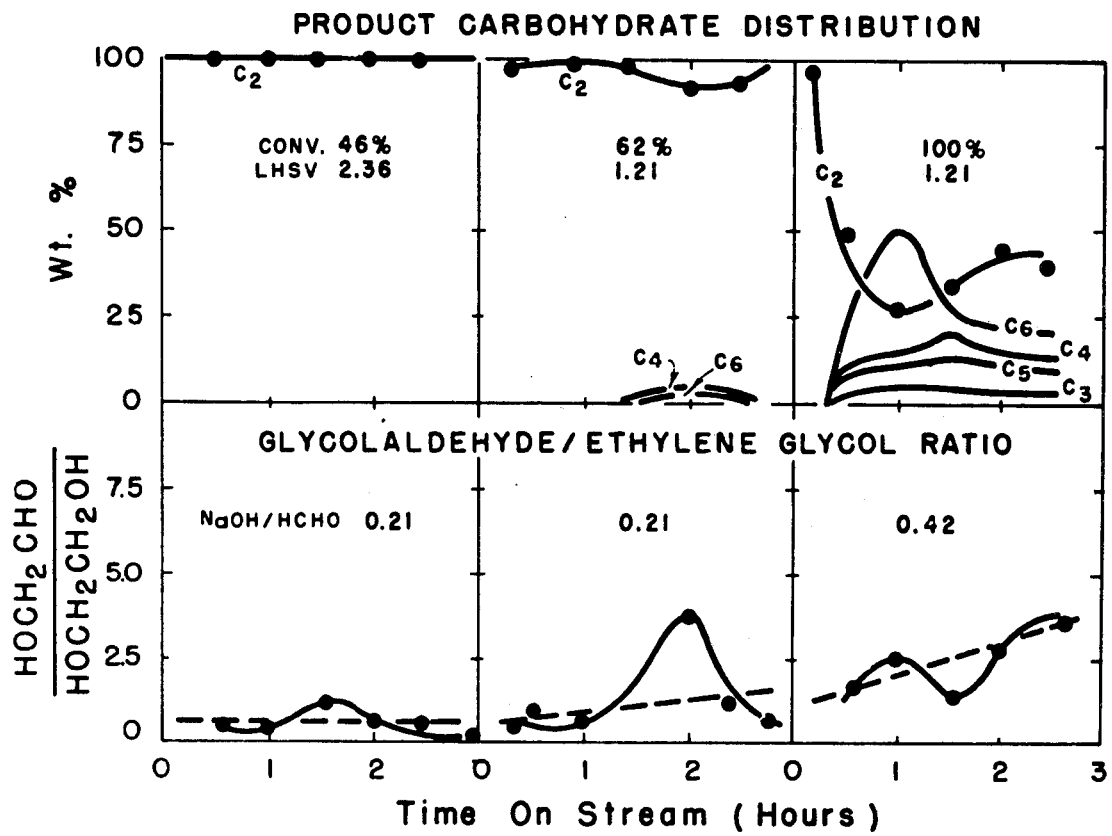
FIG. 5
EFFECT OF CONVERSION ON PRODUCT FROM 5A AT 94°C
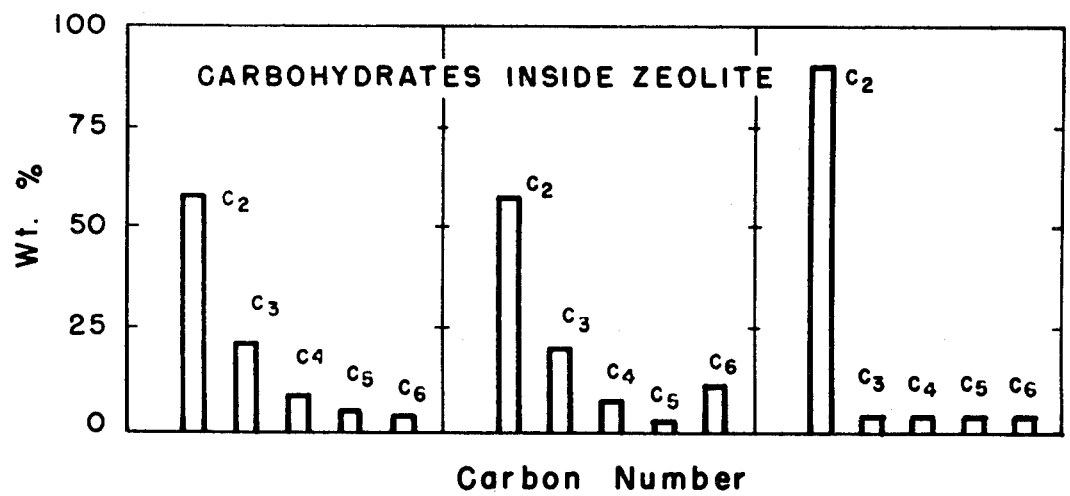

GLYCOLALDEHYDE OR ETHYLENE GLYCOL FROM FORMALDEHYDE

This is a division of application Ser. No. 38,794, filed May 14, 1979, now U.S. Pat. No. 4,238,418.

BACKGROUND OF THE INVENTION

Ethylene glycol is produced industrially from petrochemical ethylene. As the cost of crude oil continues to rise, this route to ethylene glycol becomes more and more impractical. Recent interest has developed around a process from synthesis gas (CO and $H_2$) to ethylene glycol over a rhodium-based catalyst, because of the expected availability of synthesis gas from coal gasification programs. Unfortunately, this process is carried out with an expensive catalyst, at high temperature (around 150° C. to 300° C.) and high pressure (around 1,000 to 15,000 psig). Glycolaldehyde could be a valuable specialty chemical, in that it is a low-molecular-weight, highly reactive species, and it is not available commercially.

These and other difficulties experienced with the prior art chemical processes have been obviated in a novel manner by the present invention.

It is, therefore, the object of this invention to provide a low-temperature, low-pressure process which uses an inexpensive catalyst to convert formaldehyde to glycolaldehyde and optionally, to ethylene glycol.

It is a further object of this invention to provide a valuable use for synthesis gas (CO and $H_2$) and thereby to encourage the development of coal gasification technology.

With the foregoing and other objects in view, which will appear as the description proceeds, the invention resides in the combination and arrangement of steps and the details of the composition hereinafter described and claimed, it being understood that changes in the precise embodiment of the invention herein disclosed may be made within the scope of what is claimed without departing from the spirit of the invention.

SUMMARY OF THE INVENTION

In general, the present invention involves a process for converting carbon monoxide and hydrogen to ethylene glycol, comprising the steps of converting carbon monoxide and hydrogen to methanol, converting methanol to formaldehyde, converting formaldehyde to glycolaldehyde, and converting glycolaldehyde to ethylene glycol.

More specifically, the invention involves a process for converting formaldehyde to glycolaldehyde, comprising the steps of exposing formaldehyde to a zeolite catalyst, and allowing the formaldehyde to react to glycolaldehyde.

The process preferably takes place in an aqueous solution, in a trickle bed reactor, at atmospheric pressure, and at approximately 94° C. Preferably the zeolite catalyst is chosen from the group consisting of zeolite x, zeolite A, and large-port mordenite. The process takes place in a basic solution, preferably at a pH of approximately eleven, and more preferably with sodium hydroxide present with the formaldehyde in a mole ratio to the formaldehyde of 0.21 to 0.85 (most preferably 0.42).

In the process the formaldehyde is exposed to the zeolite at a liquid hourly spaced velocity equivalent to from 1.21 to 2.36 (preferably 2.36) at 16 wt. % aqueous solution of formaldehyde over 18 gms of catalyst.

BRIEF DESCRIPTION OF THE DRAWINGS

The character of the invention, however, may be best understood by reference to one of its structural forms, as illustrated by the accompanying drawings, in which:

FIG. 5 is a graphical presentation of data which shows product distributions from reaction of NaOH/HCHO solutions at 94° C. over 5A zeolite. The effect of increasing conversion also is shown.

DESCRIPTION OF THE PREFERRED EMBODIMENT

Figure 1:
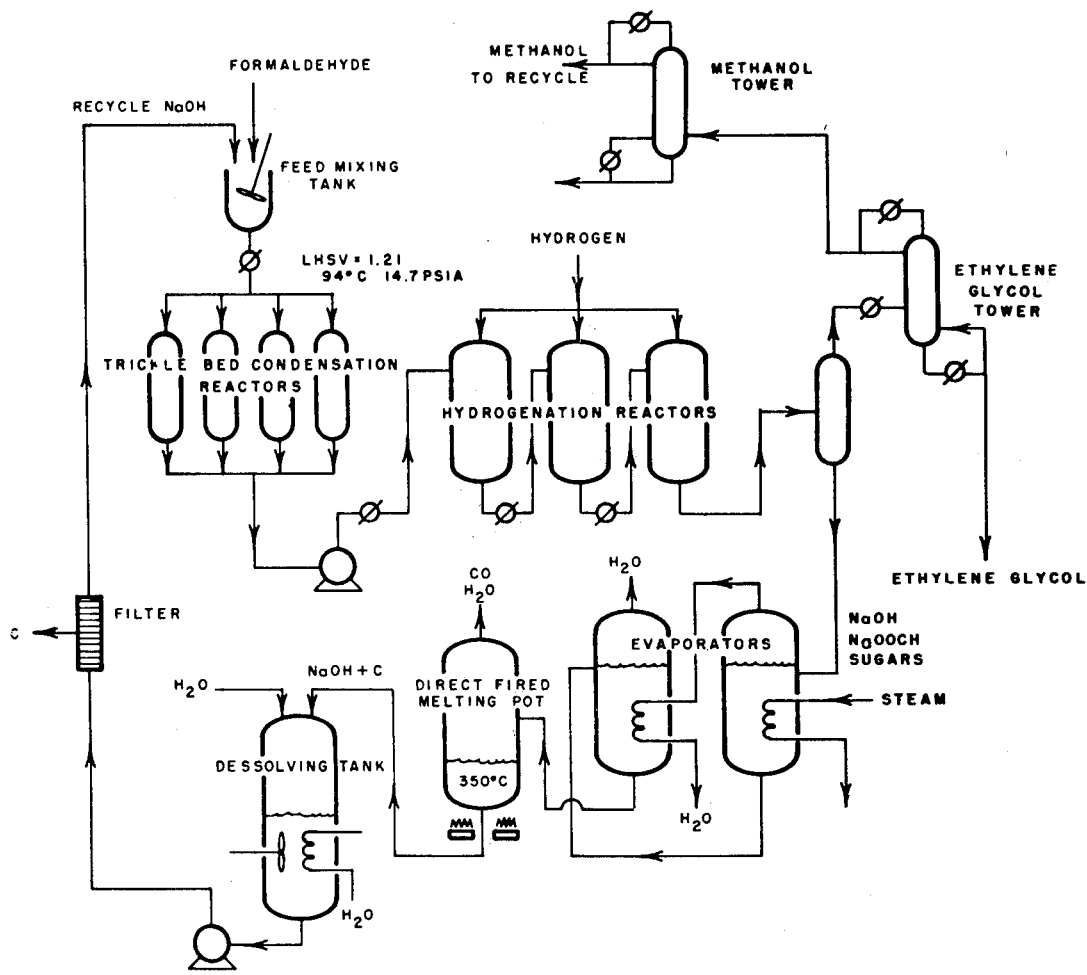
FIG. 1 is a flow chart showing the process of the present invention used to convert HCHO to ethylene glycol. NaOOCH is decomposed to NaOH for recycle if no market for NaOOCH is available; and $C_3$ and heavier byproduct sugars are carbonized.

The main reactions that take place in this NaOH-HCHO-zeolite system are as follows:

1. Formose condensation to glycolaldehyde

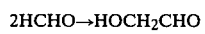
$$2HCHO \rightarrow HOCH_2CHO$$

2. Formose condensation to $C_3$ & formose sugars

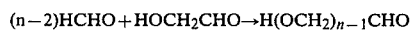
$$(n-2)HCHO + HOCH_2CHO \rightarrow H(OCH_2)_{n-1}CHO$$

3. Cannizzaro reaction of formaldehyde

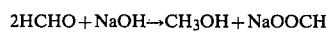
$$2HCHO + NaOH \rightarrow CH_3OH + NaOOCH$$

4. Cross-Cannizzaro reaction to ethylene glycol

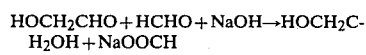
$$HOCH_2CHO + HCHO + NaOH \rightarrow HOCH_2CH_2OH + NaOOCH$$

The goal of this process is to promote reaction 1, and suppress reactions 2 and 3. Whether reaction 4 is to be promoted or suppressed will depend on the economics of reaction 4 versus hydrogenating glycolaldehyde to ethylene glycol directly. If glycolaldehyde is the desired product, then reaction 4 should be suppressed.

In the experimental work, a 30% aqueous solution of Aldrich Chemical Co. para-formaldehyde and an equal volume of NaOH solution were passed over three types of molecular sieves: 5A, NaX(13X), and Na mordenite. 5A (zeolite A) and 13X (zeolite X) beads were received from Linde Division, Union Carbide Corp. Na-mordenite (large-port mordenite) was supplied by the Norton Company as 1/16" extrudate.

The experimental procedure was described in detail by Trigerman, et al. (Sh. Trigerman, E. Biron, A. H. Weiss, React. Kin. Catal. Lett., 6 No. 3, 269 (1977)). Briefly, a 1.0 cm ID trickle-bed reactor was loaded with 18 gm of catalyst positioned between 22 cm inlet 18 cm outlet beds of 0.6 cm diam. quartz beads, heated to reaction temperature under a stream of nitrogen, and maintained in this condition for 12 hours before starting the reaction. The 35" long reaction tube was positioned inside a 7/8" OD nichrome wrapped glass tube, which was in a 2" OD glass tube. The annulus inside the outer tube served as an insulating space, and the annulus outside the inner tube prevented localized overheating by the nichrome wires. A. Harvard Instrument Co. syringe pump fed the NaOH and HCHO solutions at equal rates from separate 50 ml Hamilton gas-tight syringes into the top of the reactor. The combined feed HCHO concentration was 16 wt.%. The product was collected at the bottom, after passing through a condenser for cooling. No gas production was found.

HCHO conversion and the extent of methanol formation by the Cannizzaro reaction were determined using a Perkin Elmer 900 thermal conductivity gas chromatograph with a 6'×⅛" Carbosieve B column at 200° C. Detector temperature was 200° C. and detector current was 150 ma.

Ethylene glycol, glycolaldehyde and higher polyols, and sugars were analyzed as trimethylsilyl (TMS) ethers, using an adaptation of Sweeley's procedure (C. C. Sweeley, R. Bentley, M. Makita, W. W. Wells, J. Am. Chem. Soc., 85, 2497 (1963)). TMS derivatives were injected into a Perkin Elmer 880 FID gas chromatograph equipped with a 3'×⅛" OV-17 packed column operated at 4 cc/min $N_2$ and programmed from 100° to 250° C. at 4° C./min. Injector and detector temperatures were 250° C. It has been shown by Weiss, et al. (A. H. Weiss, R. B. LaPierre, J. Shapira, J. Catal., 16, 332 (1970)) that peak area is proportional to weight % of each carbohydrate. Table 1 lists the retention times of authentic TMS derivatives and retention time groupings that were used to establish carbon-number distributions.

Liquid product from the reactor was quickly neutralized and then evaporated over steam. The more or less water-free product was exposed to vacuum for about 10 minutes to remove residual water and to form a solid product with a large surface area. The reaction mixture used to form the derivative was a solution of 10 parts pyridine, 4 parts hexamethyl-disilazane and 2 parts trimethylchlorosilane; 1 cc of this mixture was added to 10 mg of dried product in a 10 dram vial and the reaction was carried out at room temperature and for a period of about 12 hours. Before injection into the gas chromatograph, the TMS-ether derivatives were extracted into hexane in order to eliminate pyridine solvent tailing. The extraction procedure of Partridge and Weiss (R. D. Partridge, A. H. Weiss, J. Chromat. Sci., 8, 553 (1970)) was followed.

The zeolites at the end of each run were dissolved in HF. After the used catalysts were intensively washed with water and wetted with a solution of 3/1 HCl to $NHO_3$, HF was added, and the vessel was cooled in an ice bath. The solution was neutralized, evaporated to dryness, exposed to vacuum for 10 minutes, the TMS-ether derivative prepared, and the derivatized sugars from the cavities of the zeolites were then analyzed.

Figure 2:
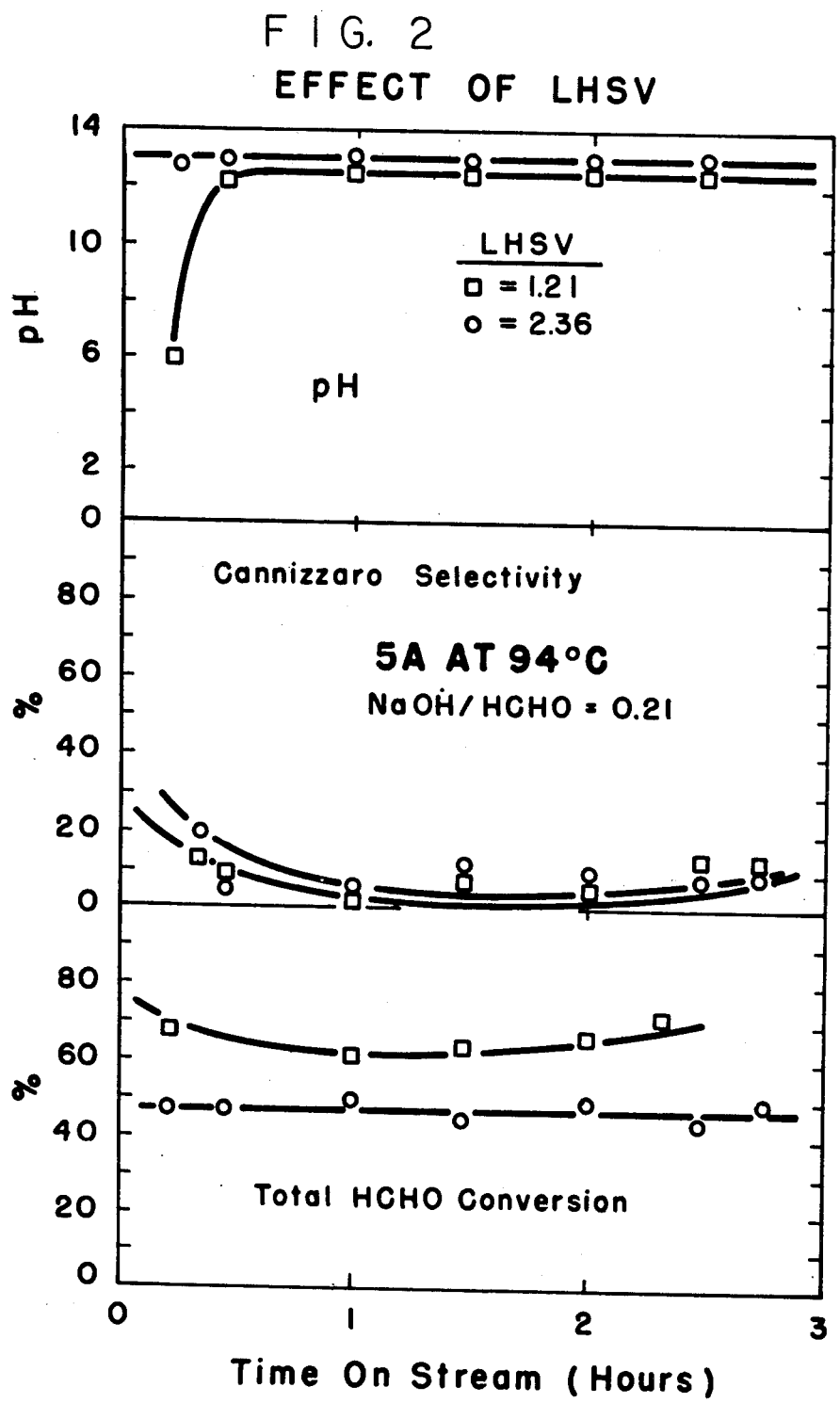
FIG. 2 is a graphical presentation of data which shows that increasing space velocity from 1.21 to 2.36 LHSV reduces total HCHO conversion but does not affect Cannizzaro selectively seriously in the NaOH/HCHO reaction over 5A Zeolite at 94° C., 0.21 NaOH/HCHO.

Experimental data are given on FIGS. 2 thru 6 as a function of time on stream, to show both transient initial and steady state activities. FIG. 2 illustrates the effect of liquid hourly space velocity (LHSV), that is, the volume of feed liquid per hour divided by the total volume of the catalyst bed including interparticle spaces. The higher the LHSV, the lower the total conversion. The selectivity to Cannizzaro reaction (and the consequent reduced product pH) are little affected by LHSV. Choice of NaOH/HCHO ratio is the key technique to minimize unwanted Cannizzarro reaction $NaOH + 2HCHO \rightarrow NaOOCH + CH_3OH$. It will be shown later that product distribution is a function of the extent of the total HCHO conversion, and hence, a function of LHSV at fixed NaOH/HCHO ratio. It is probable that 5 A exchanged to the sodium form in the course of the experiments using it.

Figure 3:
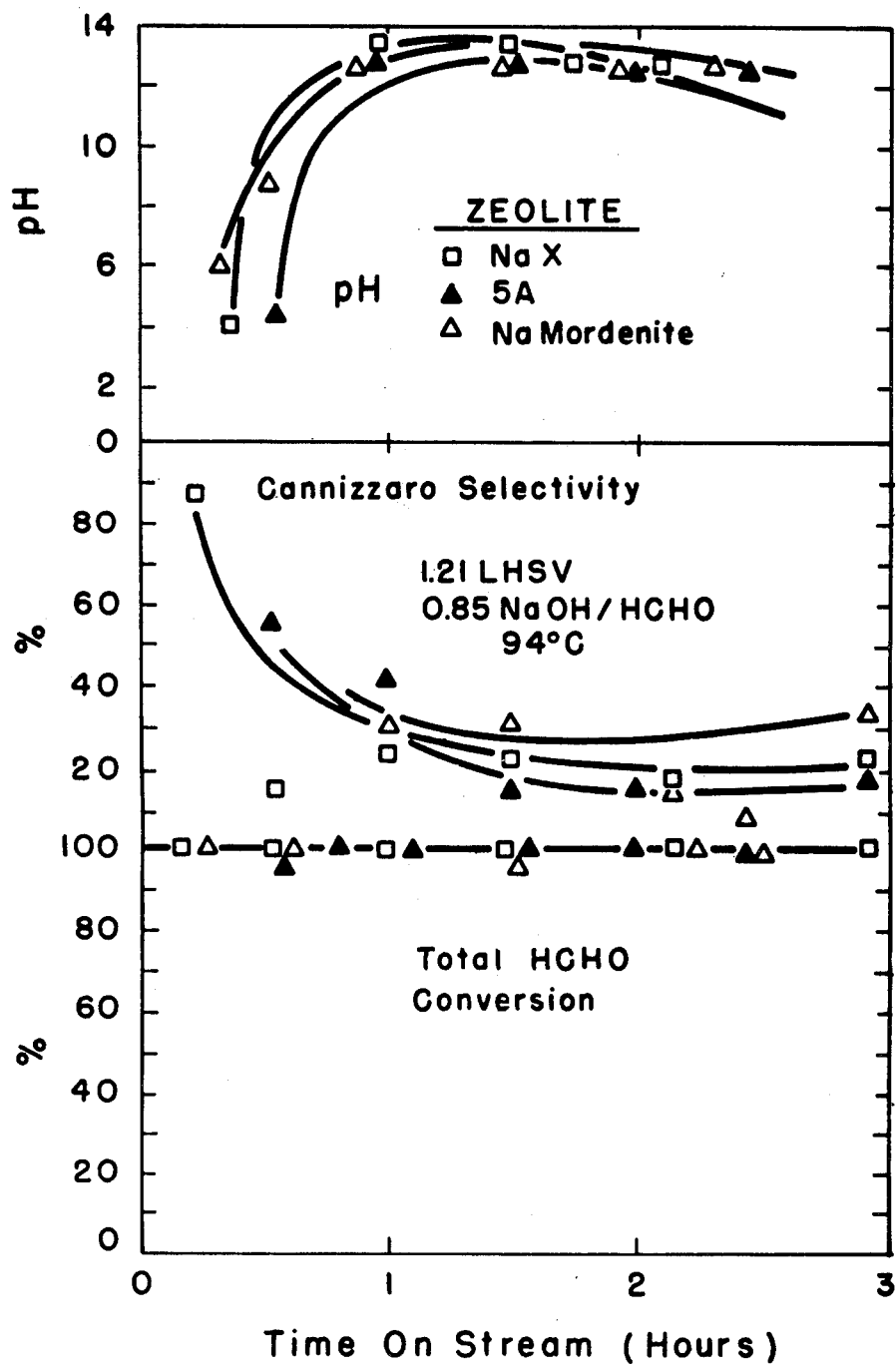
FIG. 3 is a graphical presentation of data which shows that zeolites 5A, NaX and Na mordenite are practically equivalent in activity and Cannizzaro selectively when operated near 100% total HCHO conversion. The higher NaOH/HCHO ratio of 0.85 resulted in about 25% Cannizzaro selectivity.

FIG. 3 compares 5 A, NaX, and Na mordenite at a fixed reaction condition of 94° C., 1.21 LHSV, and 0.85 NaOH/HCHO ratio. Total HCHO conversion at this condition approximated 100% for all of the zeolites. Because of the high NaOH/HCHO ratio of 0.85, Cannizzaro selectivity is high (~25%).

Figure 4:
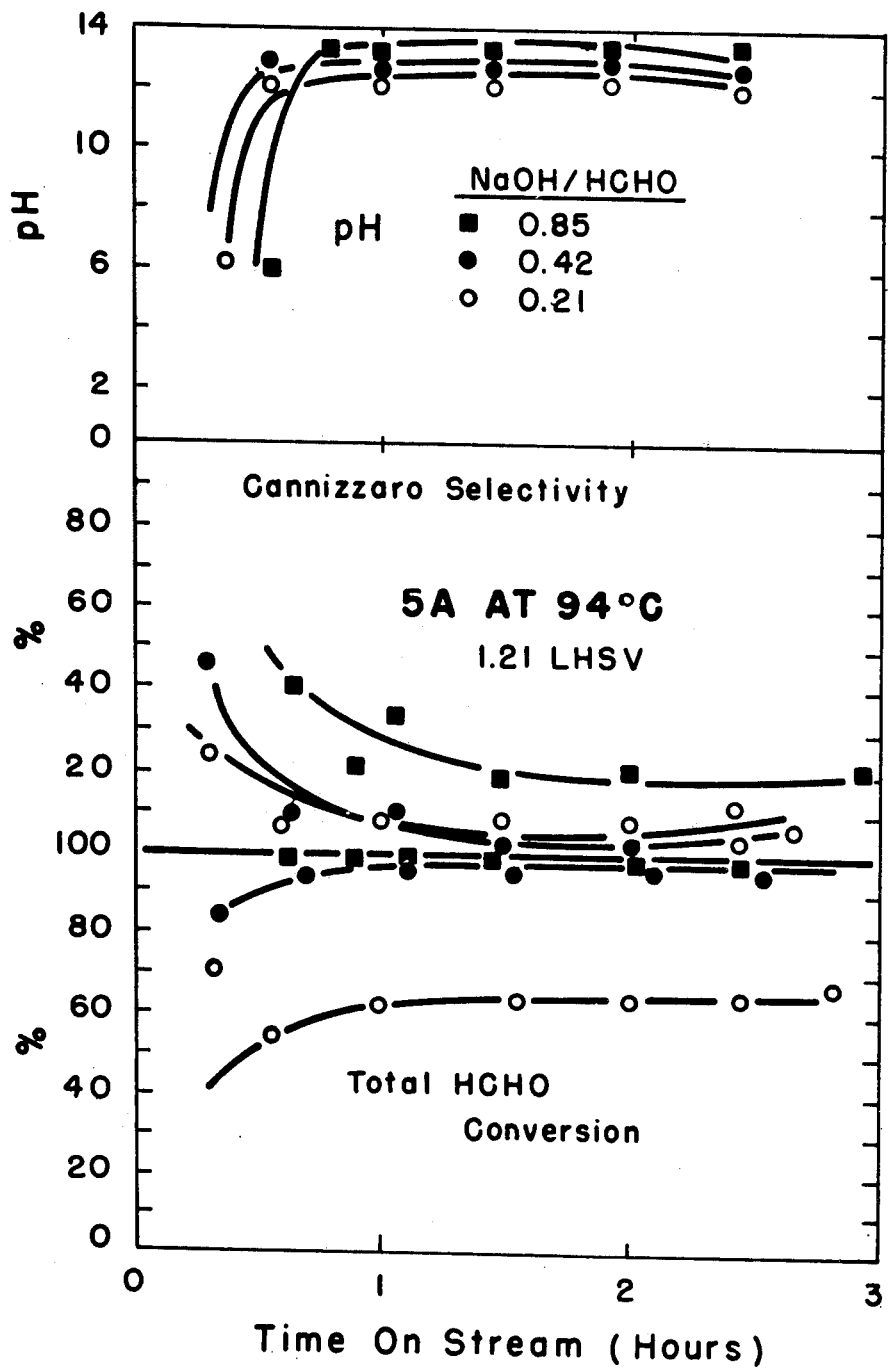
FIG. 4 is a graphical presentation of data which shows that there is an optimal NaOH/HCHO ratio to minimize undesired Cannizzaro selectivity and to maintain operation near 100% total HCHO conversion over 5A at 94° C., 1.21 LHSV.

FIG. 4 shows that for 5 A at 94° C., 1.21 LHSV, NaOH/HCHO ratio is the key variable to maintain the total conversion of HCHO near 100% and, at the same time, minimize Cannizzaro selectivity to less than ten percent.

Table 2 lists the product carbohydrate carbon number distributions as a function of time on-stream and the operating conditions and catalysts that correspond to the analyses. Table 2 shows that, at least initially, only $C_2$ species are produced. These $C_2$ species are actually a mixture of ethylene glycol and glycolaldehyde, due to the favorable alkaline environment for cross-Cannizzaro reaction to proceed.

$HCHO + HOCH_2CHO + NaOH \rightarrow NaOOCH + HOCH_2CH_2OH$

The ratio of glycolaldehyde/ethylene glycol is a measure of cross-Cannizzaro reaction extent. It is desirable to maximize this ratio, which is plotted on FIGS. 5 and 6, because, even if reduction of glycolaldehyde to ethylene glycol is desired, it will most probably be more economically advantageous to do this in an external hydrogenation process:

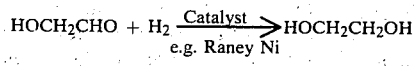

Experimental data or conditions are not available for glycolaldehyde hydrogenation. The procedures reported by Wisniak, et al. (J. Wisniak, M. Hershkowitz, R. Leibowitz, S. Stein, Ind. Eng. Chem., Prod. Res. Dev., 13, No. 1, 75 (1974)) for xylose hydrogenation over Raney Ni or by Brahme and Doralswamy (P. H. Brahme, L. K. Doralswamy, Ind. Eng. Chem., Proc. Des. Dev. 15, No. 1, 130 (1976)) for glucose hydrogenation over Raney Ni may be applicable here, but experimental demonstratration for glycolaldehyde is required.

Figure 6:
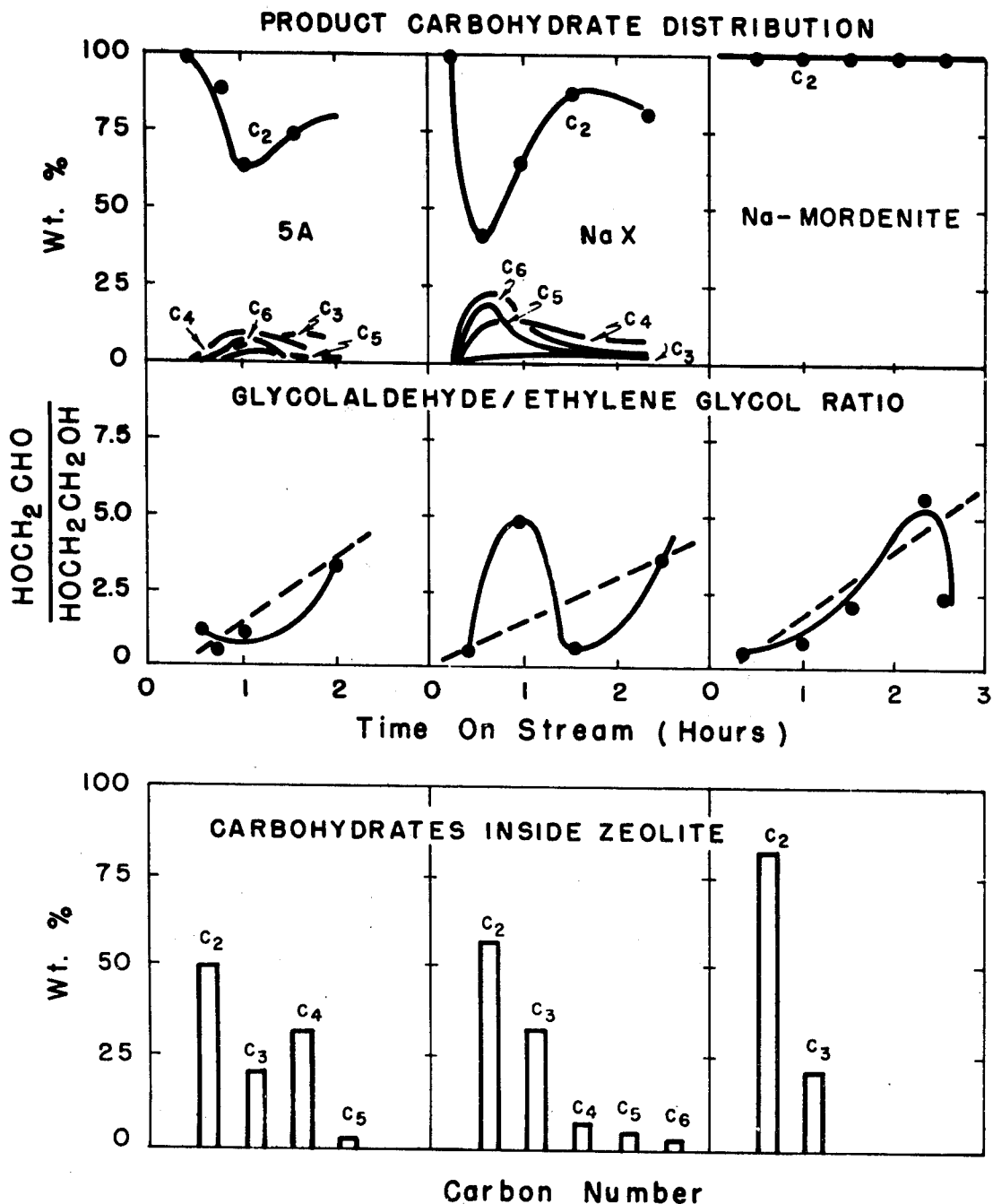
FIG. 6 is a graphical presentation of data which shows a comparison of product distributions from reaction of 0.85 NaOH/HCHO solution at 94° C., 1.21 LHSV, and 100% total HCHO conversion over 5A, NaX, and Na mordenite.

FIGS. 5 and 6 show that increasing conversion at 94° C. from 46% over 5 A to 100% over 5 A, NaX and Na mordenite increased the glycolaldehyde/ethylene glycol ration from 0.3 to 3.0. Higher severities, (i.e., lower LHSV in connection with optimal NaOH/HCHO ratio) are more favorable in minimizing cross-Cannizzaro reactions. HCHO usage in cross-Cannizzaro reation is one mole per mole of glycol formed, and is an undesirable non-selective loss of HCHO, unless the conversion of glycolaldehyde to ethylene glycol is done intentionally by cross-Cannizzaro reaction. If such is the case, it is recommended that a separate non-catalytic reaction be pursued in the range of pH 12–13.

Table 2 and FIGS. 2 and 5 show that, within analytical accuracy, 5 A catalyst can be operated to produce only $C_2$ species at 94° C., 0.21 NaOH/HCHO, and 1.21 to 1.36 LHSV (46%–62% total HCHO conversion) in a manner in which HCHO converted by Canizzaro is only 5–10%, but cross-Cannizzaro reactions are high: 0.5–1 $HOCH_2CHO/HOCH_2CH_2OH$ ratio. FIGS. 4, 5, and 6 show that if conditions are forced to 100% conversion over 5 A at 94° C., these non-selective reactions decrease, (~5% Cannizzaro and a glycolaldehyde/ethylene glycol ratio of 4), but about 20% carbohydrates of higher molecular weight are also formed as the 5 A catalyst approaches steady state. The formation of higher carbohydrates (formose sugars) reduces the overall selectivity of HCHO to $C_2$ species.

FIG. 6 compares products from 5 A, NaX, and Na mordenite at a high severity operation—0.85 NaOH/HCHO, 1.21 LHSV, and 94° C. One hundred percent conversion is had in all cases. NaX behaves similarly to 5 A, in that about 80% of the carbohydrates are selectively $C_2$. However, Na mordenite is unique in that $C_2$ carbohydrates are produced at 100% HCHO conversion in the absence of other carbohydrates. There are no product loses to higher molecular weight species, cross-Cannizzaro reaction is minimal ($HOCH_2CHO/HOCH_2CH_2OH=6$), but HCHO lost to Canizzaro reaction is ~25%.

Note that in all of the plots of $HOCH_2CHO/HOCH_2CH_2OH$ ratio shown in FIGS. 5 and 6, the ratio appears to be increasing with time and does not appear to be at steady state. Perhaps, in longer periods of time, the ratio will be so high that the cross-Canizzaro reaction will become unimportant. Experiments of longer duration than those given here are of course, required to demonstrate this point, as well as to document catalyst deactivation.

FIGS. 5 and 6 also show bar graphs of the formose sugar distributions found inside the catalysts at the end of experiments. The significant amounts of $C_3$, $C_4$, $C_5$, and $C_6$ sugars detected after dissolution of the washed 5 A and NaX suggest that the formose condensation reaction proceeded inside the cavity and that the sugars formed were too large to exit. An X-ray diffraction pattern showed a slight loss of crystallinity in the 13 X, which could be due to bulky molecules blocking the pores. Cross-Cannizzaro reaction also occurs extensively inside the zeolite cavities. Table 2 shows that $HOCH_2CHO/HOCH_2CH_2OH$ ratios were quite low inside the catalyst specimens that were analyzed, 0.07 to 0.3.

Only $C_2$ and $C_3$ species were found inside the Na mordenite cavity, but it would seem that formose sugars must form if precursors such as these are inside the mordenite pore. It may be possible, as suggested by Bierenbaum, et al. (H. S. Bierenbaum, R. D. Partridge, A. H. Weiss, Adv. in Chem. Series No. 121 "Molecular Sieves", pp 605–617 (1973)) in separate studies on cumene cracking over H-mordenite, that the activity of Na mordenite is at the pore mouth and HCHO is really not inside. Alternatively, since the pores were not filled with terminal products, one could also conclude that entry of HCHO and egress of $C_2$'s from mordenite are very rapid processes. However, th $HOCH_2CHO/HOCH_2CH_2OH$ ratio inside the mordenite of 0.150 did not differ greatly from that measured for the other catalysts, 0.07–0.30 (see Table 2), suggesting just as intense a cross-Cannizzaro activity for molecules of glycolaldehyde inside mordenite as for molecules of glycolaldehyde inside 5 A or NaX.

FIG. 1 show a process concept for producing glycolaldehyde, ethylene glycol and various side products from formaldehyde. Glycolaldehyde is a very reactive species, not currently commercially available. If a commercial process for it were developed, byproduct ethylene glycol, methanol, sodium formate, and carbohydrates could either be sold, or methanol recycled to the formaldehyde plant and sodium formate converted to NaOH for recycle. Ethylene glycol could be the major product by reacting the mixture with HCHO and NaOH for cross-Cannizzaro conversion of the glycolaldehyde to ethylne glycol. Possibly preferable, for economic reasons, would be catalytic hydrogenation of the product glycolaldehyde to ethylene glycol. The net effect is that ethylene glycol can be produced selectively from formaldehyde in this system. Such a process has not been developed, but we shall now desscribe what it may be and the type of problems that will occur.

FIG. 1 is a conceptual process flow sheet for ethylene glycol manufacture. Formalin solution from a formaldehyde plant is mixed with NaOH solution and heated to process temperature, 94° C. This solution is then pumped at 1.21 LHSV into parallel trickle bed condensation reactors at atmospheric pressure. The formaldehyde reacts to 100% conversion over zeolite catalyst. The condensation reaction 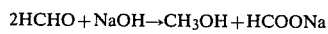 $2HCHO \rightarrow HOCH_2 CHO$ is 75% selective and competes with the Cannizzaro reaction:

$$2HCHO + NaOH \rightarrow CH_3OH + HCOONa$$

The Canizzaro selectivity is 24% and it should be assumed that there is at least 1% selectivity to sugars. Both reactions are liquid phase in a trickle bed reactor, using sodium mordenite as a catalyst. Sodium hydroxide is necessary to prevent formic acid from destroying the zeolite catalyst.

The output of the condensation reactors is then used as feed for the hydrogenation step, where the glycolaldehyde/ethylene glycol mixture is hydrogenated at 125° C., 400 psig over nickel catalyst to ethylene glycol. Three reactors in series, with interstage cooling, are suggested for hydrogenation. This hydrogenation reaction has not yet been carried out.

The product from the hydrogenation reactors is separated, e.g., by extraction, and ethylene glycol and lighter are recovered. Inorganics and sugars are combined in water solution. Methanol is recycled back to the formaldehyde process.

The liquid product from the separation step is sodium hydroxide solution, with sodium formate and non-selectively formed $C_3$ and higher sugars and enough water so that the stream will flow as a liquid. This mixture is evaporated and melted. Upon melting, the sodium formate (mp 253° C.) decomposes spontaneously to sodium hydroxide (mp 318.4° C.) and carbon monoxide.

$NaOOCH \rightarrow NaOH + CO$

Thus, all of the reacted sodium hydroxide is recovered for recycle. This reaction is spontaneous upon melting, and is also quite exothermic. The carbon monoxide and steam given off during operation can either be appropriately disposed of as waste gas, or dried and sent back "over the fence" to a methanol plant where it can be used as raw material.

Formose sugars will thermally decompose in the melter to carbonaceous materials. For example, a simplification of glucose decomposition is $$C_6(H_2O)_5 \xrightarrow{\Delta} 6C + 5H_2O$$

This carbon will be in the NaOH from the melter. The NaOH which is flaked and reconstituted into a recycle stream, can then be filtered before recycle to separate and reject not only the carbon but also solution wetting it, thereby preventing accumulation of impurities in the system.

The only experimentation pursued at this point is the reaction over zeolites. The separation and thermal decomposition steps require experimental demonstration in a development program.

TABLE 1
RETENTION TIMES FOR AUTHENTIC TMS-CARBOHYDRATES AND RETENTION TIME INTERVALS FOR CARBON-NUMBER GROUPINGS

| TMS Ether of Carbohydrate | Retention Time, Seconds |
|---|---|
| Ethylene Glycol | 80 |
| Glycolaldehyde | 90–120 |
| Dihydroxyoaetone | 231 |
| Hydroxymethyl-glyceraldehyde | 281 |
| Erythrose | 310 |
| Arabinose | 398 |
| D-xylose | 480 |
| Mannose | 508–556 |
| Sorbose | 500,538,602 |
| Fructose | 549 |
| α-Glucose | 562 |
| β-Glucose | 618 |
| Sucrose | 969 |
| D-Galactose | 568 |
| C 2 | 100–120 |
| C 3 | 200–250 |
| C 4 | 250–380 |
| C 5 | 400–500 |
| C 6 | 500–630 |
| C 7 | 630–800 |

TABLE 2
Carbohydrate Analyses at Various Times On-Stream, Trickle Bed Reaction at 94° C.

| Type of Zeolite | NaOH/HCHO Mole Ratio | LHSV | Time On-Stream (hours) | $C_2$ | $C_3$ | $C_4$ | $C_5$ | $C_6$ | $C_7$ | Ratio Inside Zeolite $HOCH_2CHO/HOCH_2CH_2OH$ |
|---|---|---|---|---|---|---|---|---|---|---|
| Na Mordenite | 0.85 | 1.21 | 0.5 | 100 | | | | | | |
| | | | 1.0 | 100 | | | | | | |
| | | | 1.50 | 100 | | | | | | |
| | | | 2.25 | 100 | | | | | | |
| | | | 2.50 | 100 | | | | | | |
| | | | 3.00 | 100 | | | | | | 0.150 |
| NaX | 0.85 | 1.21 | 0.25 | 100 | | | | | | |
| | | | 0.50 | 38.56 | 0.41 | 13.81 | 21.30 | 25.47 | 0.45 | |
| | | | 1.00 | 61.30 | 0.59 | 13.52 | 5.12 | 14.13 | 4.34 | |
| | | | 1.50 | 89.50 | 1.11 | 4.24 | 1.70 | 1.62 | 1.37 | |
| | | | 2.25 | 80.20 | 2.17 | 6.36 | 5.26 | 5.54 | 0.00 | 0.071 |
| 5A | 0.85 | 1.21 | 0.50 | 100 | | | | | | |
| | | | 0.75 | 90.63 | 2.5 | 5.12 | 0.63 | 1.12 | | |
| | | | 1.00 | 63.8 | 8.58 | 10.11 | 7.42 | 10.10 | | |
| | | | 1.50 | 76.38 | 9.74 | 8.42 | 3.78 | 1.67 | | 0.301 |
| 5A | 0.42 | 1.21 | 0.25 | 100 | | | | | | |
| | | | 0.50 | 53.29 | 1.35 | 12.55 | 5.96 | 26.84 | | |
| | | | 1.00 | 25.29 | 3.53 | 11.90 | 8.40 | 50.23 | 0.63 | |
| | | | 1.50 | 30.05 | 1.97 | 23.04 | 13.26 | 24.50 | 7.17 | |
| | | | 2.00 | 48.20 | 2.79 | 16.10 | 9.97 | 10.32 | 2.61 | |
| | | | 2.50 | 41.70 | 1.89 | 17.91 | 9.35 | 24.77 | 4.38 | 0.270 |
| 5A | 0.21 | 1.21 | 0.25 | 100 | | | | | | |
| | | | 0.50 | 100 | | | | | | |
| | | | 1.00 | 100 | | | | | | |
| | | | 1.50 | 100 | | | | | | |
| | | | 2.00 | 90.0 | 0.00 | 5.29 | 0.71 | 0.71 | 4.0 | |
| | | | 2.50 | 93.9 | 0.00 | 2.71 | 0.59 | 0.59 | 2.74 | 0.300 |
| | | | 2.75 | 100 | | | | | | |
| 5A | 0.21 | 2.36 | 0.5 | 100 | | | | | | |
| | | | 1.0 | 100 | | | | | | |
| | | | 1.5 | 100 | | | | | | |
| | | | 2.0 | 100 | | | | | | |
| | | | 2.5 | 100 | | | | | | |
| | | | 2.8 | 100 | | | | | | 0.290 |

While it will be apparent that the illustrated embodiments of the invention herein disclosed are well calculated adequately to fulfill the objects and advantages primarily stated, it is to be understood that the invention is susceptible to variation, modification, and change within the spirit and scope of the subjoined claims.

The invention having been thus described, what is claimed as new and desired to secure by Letters Patent is:

1. A process for converting carbon monoxide and hydrogen to ethylene glycol, comprising the steps of:
   (a) converting carbon monoxide and hydrogen to methanol,
   (b) converting methanol to formaldehyde,
   (c) converting formaldehyde to glycolaldehyde,
   (d) converting glycolaldehyde to ethylene glycol by exposing glycolaldehyde and formaldehyde to a zeolite catalyst in an aqueous basic solution including sodium hydroxide in a mole ratio to the glycolaldehyde of 0.21 to 0.85, and
   (e) maintaining the above ratio at approximately 94° C. and at atmospheric pressure.

2. A process as recited in claim 1, wherein the glycolaldehyde is exposed to the zeolite at a liquid hourly space velocity of approximately 1.21.

3. A process as recited in claim 1, wherein the reaction in step (d) takes place in a trickle bed condensation reactor and results in an output mixture of glycolaldehyde and ethylene glycol.

4. A process as recited in claim 3, wherein the output mixture from the trickle bed condensation reactor is passed through a hydrogenation reactor in which the mixture is hydrogenated at 125° C., 400 psig over a nickel catalyst for additional conversion of glycolaldehyde to ethylene glycol.

5. A process as recited in claim 14, wherein the output mixture from the trickle bed reactor is passed through three hydrogenation reactors in series.

6. A process as recited in claim 5, wherein the output mixture is cooled to substantially below 94° C. between said hydrogenation reactors.

7. A process as recited in claim 6, wherein ethylene glycol is separated from the product mixture from the hydrogenation reactor.

8. A process as recited in claim 1, wherein the zeolite is sodium mordenite.

* * * * *